(12) United States Patent
Soe

(10) Patent No.: US 8,663,628 B2
(45) Date of Patent: Mar. 4, 2014

(54) SOLID PHASE GLYCEROLYSIS

(75) Inventor: Jorn B. Soe, Tilst (DK)

(73) Assignee: Dupont Nutrition Biosciences APS, Copenhagen K (DK)

( * ) Notice: Subject to any disclaimer, the term of this patent is extended or adjusted under 35 U.S.C. 154(b) by 1157 days.

(21) Appl. No.: 12/129,968

(22) Filed: May 30, 2008

(65) Prior Publication Data

US 2008/0233235 A1 Sep. 25, 2008

Related U.S. Application Data

(62) Division of application No. 10/343,490, filed as application No. PCT/IB01/01830 on Aug. 2, 2001, now abandoned.

(30) Foreign Application Priority Data

Aug. 3, 2000 (GB) .................................. 0019118.9

(51) Int. Cl.
*A61K 38/43* (2006.01)

(52) U.S. Cl.
USPC .......................................... 424/94.1; 426/33

(58) Field of Classification Search
None
See application file for complete search history.

(56) References Cited

U.S. PATENT DOCUMENTS

| 4,178,393 A | 12/1979 | Gregersen |
| 5,993,806 A | 11/1999 | Galle |
| 2003/0180417 A1 | 9/2003 | Soe |

FOREIGN PATENT DOCUMENTS

EP 0 445 692 A 11/1991

OTHER PUBLICATIONS

McNeill et al, "Solid Phase Enzymatic Glycerolysis of Beef Tallow Resulting in a High Yield of Monoglyceride", JAOCS, vol. 67, No. 11, Nov. 1990, pp. 779-783.
McNeill et al, "Further Improvements in the Yield of Monoglycerides During Enzymatic Glycerolysis of Fats and Oils", JAOCS, vol. 68, No. 1, Jan. 1991, pp. 6-10.
Bitman et al, "Changes in Milk Fat Phospholipids During Lactation", 1990 J Dairy Sci 73:1208-1216.
Ernst et al, Profiles in Agricultural Entrepeneurship, Aug. 2000, pp. 1-8 http://www.uky.edu/Ag/AgEcon/pubs/ext_aec/ext2001-05.pdf.

*Primary Examiner* — Irene Marx
(74) *Attorney, Agent, or Firm* — Nixon & Vanderhye P.C.

(57) ABSTRACT

An enzymatic solid phase reaction for preparing a solid having greater than 40% monoglyceride from a reaction mixture; wherein the reaction mixture comprises: (i) lipase; (ii) at least 14 weight % glycerol; and (iii) glyceride; and optionally (iv) lecithin; such that if (iv) is not present then the glyceride (iii) has an iodine value of between about 5 and about 35, and a solid fat content of more than about 75% at 20° C. The present invention further relates to a process of preparing an enzymatic solid phase reaction mixture for preparing a solid having greater than 40% monoglyceride.

11 Claims, 2 Drawing Sheets

Figure 1:
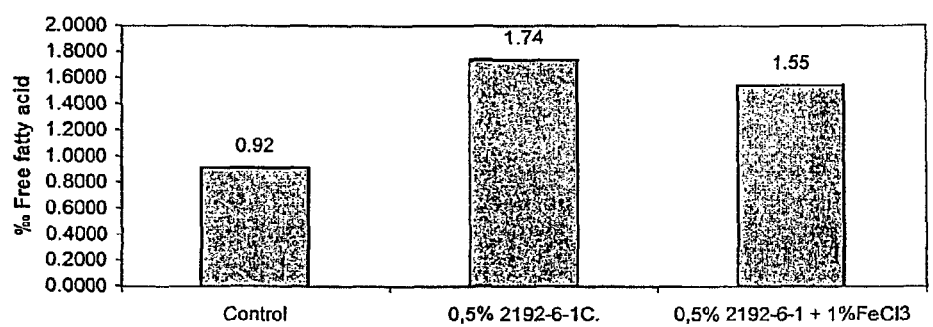

|  | | 1 | 2 | 3 | 4 | 5 |
|---|---|---|---|---|---|---|
| Hardened Palm Stearin | g | 7 | 8 | 9 | 9,5 | 9,9 |
| Lecithin powder, 074793 | g | 3 | 2 | 1 | 0,5 | 0,1 |
| Glycerol, 99,5% | g | 2 | 2 | 2 | 2 | 2 |
| Lipase #2402 | g | 0,01 | 0,01 | 0,01 | 0,01 | 0,01 |
| Water | g | 0,05 | 0,05 | 0,05 | 0,05 | 0,05 |

SOLID PHASE GLYCEROLYSIS

The present application is a divisional of application Ser. No. 10/343,490, filed Apr. 25, 2003 (abandoned), which is a U.S. 371 National Phase of PCT/IB01/01830, filed 2 Aug. 2001, which claims benefit of GB0019118.9, filed 3 Aug. 2000, the entire contents of each of which is hereby incorporated herein by reference.

The present invention relates to a combination of active ingredients for use in the food industry. In particular, the invention relates to a solid phase glycerolysis reaction that yields products having a surprisingly high level of monoglyceride.

Lipase has been used in the baking industry over a number of years and a variety of different applications have been developed. However, studies have revealed that in certain applications there are often drawbacks associated with the use of lipase. In particular, one of the limiting factors for the use of lipase in bread-making is that certain substrates, such as wheat flour, only contain approximately 2% lipids, of which only part is available for enzymatic attack. Recent research has therefore focussed on the possibility of combining lipase with a lipid in order to improve the benefit from using lipase in bread-making.

European Patent Application No. 0585988 (Gist Brocades) discloses that an improved anti-staling effect is obtained when lipase is added to dough, as a result of monoglyceride formation. However, it has been shown that the level of monoglyceride only increases by a marginal amount (WO 98/45453, Danisco A/S) since the lipase added to the dough can also readily degrade the monoglyceride to glycerol and free fatty acid. This effect is observed for doughs that contain only endogenous lipids, as well as for doughs containing added fat/oil.

It is well known that some lipases are able to work in very low water environments. McNeill et al, [JAOCS, Vol. 68, no. 1 (January 1991), 1-5], Bornscheuer et al, [Enzyme and Microbial Technology, 17: 578-586, 1995] and Thide et al [JAOCS, Vol. 71, no. 3 (March 1994), 339-342] have shown that it is possible to carry out glycerolysis reactions in mixtures of fat/oil and glycerol by adding specific lipases and allowing the glycerolysis reaction to take place below the melting point of the fat/oil. However, McNeill et al have also demonstrated that it is considerably more difficult to carry out glycerolysis in the solid phase with fully hardened fat, such as hydrogenated tallow.

The present invention seeks to address the problems encountered in the above-mentioned prior art processes. In particular, the invention seeks to improve the yield of monoglyceride and alleviate the problems associated with carrying out glycerolysis with hardened fats.

Thus, in the broadest sense, the present invention provides an enzymatic solid phase reaction for preparing a solid having greater than 40% monoglyceride by combining hardened fat, glycerol, lipase and optionally lecithin.

More specifically, the present invention provides an enzymatic solid phase reaction for preparing a solid having greater than 40% monoglyceride from a reaction mixture;
wherein the reaction mixture comprises
  (i) lipase;
  (ii) at least 14 weight % glycerol; and
  (iii) glyceride;
and optionally
  (iv) lecithin;
such that if (iv) is not present then the glyceride (iii) has an iodine value of between about 5 and about 35, and a solid fat content of more than about 75% at 20° C.

In particular, the invention provides a mixture of hardened fat, glycerol, lipase, and optionally lecithin, that can be made into a powder and stored under controlled temperature conditions. The glycerolysis reaction may then take place in powdered form.

In this way, it is possible to obtain a powdered product containing a high level of monoglyceride, an active lipase, and optionally lecithin. Such reaction products are of commercial interest in the bread-making industry as monoglyceride is known to make a significant contribution to anti-staling. In addition, the lecithin (if present) contributes to dough strengthening, whilst the lipase contributes to improved dough stability and crumb structure.

The solid phase reaction mixture of the present invention comprises glyceride.

In a preferred embodiment, the glyceride is present in the reaction mixture in an amount from about 1% to about 86% by weight.

In a first preferred aspect, the solid phase reaction mixture of the invention comprises lecithin. In the presence of lecithin, the glyceride of the reaction mixture may be any hardened fat, including fully hardened fat.

The term "hardened fat" or "hydrogenated fat" is fat that has been exposed to a hydrogenation process (Ullmanns Encyclopedia of Industrial Chemistry, Sixth Edition, Fats and Fatty Oils, 4.3 and 8). Typically, the fat is subjected to catalytic hydrogenation in the presence of a transition metal catalyst, for example, a nickel, palladium or platinum catalyst.

Fully hardened fat is defined as a fat having an Iodine Value (IV) of less than 5, where the iodine value is measured by the conventional IUPAC technique (International Union of Pure and Applied Chemistry (IUPAC), Standard Method for the Analysis of Oils, Fats and Derivatives, Method 2.205).

It is to be noted that the prior art has neither disclosed nor suggested the use of lecithin to achieve a product having a high monoglyceride content from a solid phase glycerolysis process.

In a second aspect, the reaction mixture of the invention does not comprise lecithin. In the absence of lecithin, the glyceride of the present reaction mixture has an iodine value of between about 5 and 35, and a solid fat content of more than about 75% at 20° C.

The term solid fat content (SFC) is defined and measured according to IUPAC Method 2.150 (International Union of Pure and Applied Chemistry (IUPAC), Standard Method for the Analysis of Oils, Fats and Derivatives). Accordingly, the term 'solid' used in relation to fats and oils means that the oil/fat in question contains solid fat according to the above-mentioned definition for solid fat content.

The "iodine value" of a glyceride or fat is that measured by the above-mentioned IUPAC method.

Thus, in order to achieve a product having greater than 40% monoglyceride, in the absence of lecithin, the glyceride component of the reaction mixture should not comprise fully hardened fat alone. Instead, to achieve a product with the desired level of monoglyceride, the glyceride component must comprise at least one unsaturated fat. In some instances, the glyceride may be an unsaturated fat, or a mixture of unsaturated fats, wherein the unsaturated fat, or mixture, has an iodine value of between about 5 and about 35. In other instances, the glyceride component may be a mixture of at least one unsaturated fat and at least one saturated fat, such that the iodine value of the mixture is between about 5 and about 35.

In a preferred embodiment of the invention, in the absence of lecithin, the glyceride component of the reaction mixture has an iodine value of between about 5 and about 25.

In a more preferred embodiment, in the absence of lecithin, the glyceride has an iodine value of between 5 and about 15. Even more preferably, in the absence of lecithin, the glyceride has an iodine value of between about 5 and about 10.

It should be noted that the prior art does not disclose solid phase glycerolysis methods that yield products with a monoglyceride content in excess of 40% and which are suitable for use with the hardened fats of the present invention. Nor does the prior art suggest suitable techniques for handling such solid phase glycerolysis reaction mixtures.

Preferably, the glyceride of the present invention is derived from palm oil, sunflower oil, rape seed oil, soya bean oil, safflower oil, cottonseed oil, ground nut oil, corn oil, olive oil, peanut oil, lard, tallow, or mixtures thereof.

In a preferred embodiment of the invention, the glyceride of the reaction mixture is a triglyceride.

In an alternative preferred embodiment, the glyceride is a diglyceride.

The term "triglyceride" preferably means a triester of glycerol and a fatty acid. More preferably the triglyceride is a triester of glycerol, and a $C_4$ to $C_{24}$ fatty acid.

Preferably, the triglyceride is selected from triglycerides having a fatty acid chain length of no greater than 14 carbons, triglycerides having a fatty acid chain length of from 4 to 14 carbons, triglycerides having a fatty acid chain length of from 6 to 14 carbons, triglycerides having a fatty acid chain length of from 8 to 14 carbons, triglycerides having a fatty acid chain length of from 10 to 14 carbons, triglycerides having a fatty acid chain length of 12 carbons, triglycerides having a fatty acid chain length of from 16 to 24 carbons, triglycerides having a fatty acid chain length of from 16 to 22 carbons, triglycerides having a fatty acid chain length of from 18 to 22 carbons, triglycerides having a fatty acid chain length of from 18 to 20 carbons, mixtures and derivatives thereof.

In a highly preferred embodiment of the invention, the triglyceride used in the reaction mixture is hardened palm stearin.

Palm stearin may be obtained by the crystallization of palm oil under controlled cooling conditions, followed by separation to yield a low-melting liquid phase (palm olein) and a high-melting solid phase (palm stearin). Further details may be found in Bailey's Industrial Oil and Fat Products, Fifth Edition, Volume 2, page 321. The term fractionated palm stearin refers to the isolated palm stearin component obtainable by such a process.

The reaction mixture of the present invention optionally comprises lecithin. In the presence of lecithin, the limiting proviso relating to the iodine value and the solid fat content (at 20° C.) of the glyceride component does not apply.

By way of definition, lecithin comprises a mixture of the diglycerides of stearic, palmitic and oleic acids, linked to a choline ester of phosphoric acid (Merck Index, $12^{th}$ Edition, 5452).

Preferably, where lecithin is present, the lecithin is selected from plant lecithin, powdered lecithin, synthetic lecithin, or hydrolysed lecithin. Preferably, the lecithin is soya lecithin.

Preferably, where lecithin is present, the lecithin is in an amount from about 1% to about 50% by weight of the total reaction mixture.

The reaction mixture of the present invention further comprises lipase. The lipase can be a wild type lipase or a mutant lipase. The lipase may be prepared by the use of recombinant DNA technology.

The lipase may be derived from a number of different sources.

Preferably, the lipase is derived from *Pseudomonas* sp., *Chromobacterium viscosum*, *Pseudomonas cepacia*, *Pseudomonas stutzeri*, *Pseudomonas flourescens*, *Mucor meihei* or *Candida antartica*.

The reaction mixture of the present invention further comprises glycerol, in an amount of at least 14 weight % of the total reaction mixture.

In a preferred embodiment, the glycerol is present in an amount from about 14% to about 25% by weight of the total reaction mixture.

More preferably, the glycerol is present in an amount from about 16% to about 19% by weight of the total reaction mixture.

The reaction mixture of the present invention may further comprise one or more additional components. Such additional components include, for example, antioxidants which improve the oxidative stability.

The reaction mixture may further comprise one or more solid carriers to aid delivery of the glycerol. Examples of suitable solid carriers include fibre, beet fibre, hydrocolloids, calcium carbonate, tricalcium phosphate, silica and fused silica.

In some cases, one of the limitations of spray crystallizing fats prior to solid phase glycerolysis is that the glycerol can make the powder slightly greasy. In order to alleviate this problem, a solid carrier for the glycerol may be added to the reaction mixture to act as a delivery system for the glycerol. One such example of a solid carrier for glycerol is sugar beet fibre, for example, Fibrex. The presence of a solid carrier allows for improved processing of the reaction mixture, which in turn leads to a better quality product. In addition, the presence of a solid carrier also allows for increased water absorption, which is advantageous in certain applications such as baking and bread-making. More specifically, increased water absorption in bread-making contributes to improved moistness and freshness of the bread.

Typically, the ingredients of the reaction mixture of the invention are processed into a solid powder and stored under controlled temperature conditions. Glycerolysis to form the desired monoglyceride product in high yield may then take place in the solid phase.

In a preferred embodiment, the monoglyceride formed in the enzymatic solid phase reaction of the invention is formed at a temperature of between −10 and 50° C.

In a highly preferred embodiment, the monoglyceride is formed at a temperature of between 25 and 45° C.

The solid phase glycerolysis product obtained from the reaction of the invention is intended for use in baking and other applications.

Generally, the lipase is still active when the solid phase glycerolysis product is used, for example, when it is added to a dough. In some instances, it is advantageous to have active lipase present. Indeed, experiments have shown that glycerolysis products prepared according to the present invention that contain active lipase are of particular interest in certain baking applications because the monoglyceride and lecithin contribute to improved softness, whilst the lipase and lecithin have a dough strengthening effect.

However, in certain other applications the level of lipase activity is often too high and may cause adverse effects. Thus, the glycerolysis product prepared from the present reaction mixture may be combined with a lipase inhibitor, for example, ferrichloride ($FeCl_3$). In this way, if necessary, the activity of the lipase can be regulated, depending on the application.

A further aspect of the invention relates to a process for preparing an enzymatic solid phase reaction mixture for preparing a solid having greater than 40% monoglyceride, said process comprising:

(i) melting a glyceride, optionally with a lecithin, to form a fat phase;
(ii) adding to said fat phase a solution of lipase in glycerol, wherein the glycerol is present in an amount of at least 14% by weight of the total mixture, and stirring the resultant mixture;
(iii) homogenising said mixture;
(iv) processing said mixture to form said enzymatic solid phase reaction mixture.

In one preferred embodiment, the reaction mixture of the present invention is subsequently spray crystallized.

Spray crystallization is a unit operation, similar to spray drying, which is used to atomise a melt. The technique uses a spray tower and will be familiar to those skilled in the relevant field. Firstly, the liquid melt is atomised by a spray nozzle or wheel to form small liquid particles. The particles are then cooled down to below their melting point by a flow of cool air in the spray tower, causing the atomised melt to crystallize as fine particles or a powder. Further reference to spray crystallization may be found in Ullmanns Encyclopedia, Sixth Edition, Crystallization and Precipitation, 10.4. Optionally, after spray crystallization the particles may be further processed by cryogenic milling.

In another preferred embodiment, the enzymatic solid phase reaction mixture of the present invention is subsequently pelletized, flaked or extruded, and optionally ground.

Pelleting is a unit operation used to obtain solid pellets from a melt. The technique is well known in the art and uses a cooled metal belt onto which the melt is deposited. Typically, the melt is deposited through a series of small holes to form small droplets that solidify on the cooling belt. Further details of pelletting may be found in Perry's Chemical Engineers' Handbook, Sixth Edition, Equipment for Fusion of Solids, p. 11-45.

Flaking is a unit operation familiar to those skilled in the relevant field that is used to obtain a solid from a melt. The technique involves crystallizing the melt onto a metal conveyer belt or a rotating drum with a cooling unit. The solidified material may then be scraped off the drum or belt with a knife. Further details of the technique are described in Perry's Chemical Engineers' Handbook, Sixth Edition, Equipment for the Fusion of Solids, p. 11-45. The material obtained from the flaking process may subsequently be converted to a powder by cryogenic milling (or low temperature grinding).

A further preferred aspect of the invention relates to a foodstuff comprising the glycerolysis product obtained by the solid phase reaction. By the term "foodstuff" we mean a substance which is suitable for human or animal consumption.

Preferably, the foodstuff comprising the glycerolysis product is selected from baked goods, including breads, cakes, sweet dough products, laminated doughs, liquid batters, muffins, doughnuts, biscuits, crackers and cookies; confectionery, including chocolate, candies, caramels, halawa, gums, including sugar free and sugar sweetened gums, bubble gum, soft bubble gum, chewing gum and puddings; frozen products including sorbets, preferably frozen dairy products, including ice cream and ice milk; dairy products, including coffee cream, whipped cream, custard cream, milk drinks and yogurts; mousses, whipped vegetable creams, meat products, including processed meat products; edible oils and fats, aerated and non-aerated whipped products, oil-in-water emulsions, water-in-oil emulsions, margarine, shortening and spreads including low fat and very low fat spreads; dressings, mayonnaise, dips, cream based sauces, cream based soups, beverages, spice emulsions, sauces and mayonnaise.

The present invention will now be described only by way of example and with reference to the accompanying figures, wherein:

FIG. 1 shows the effect of adding the solid phase glycerolysis product (2192-6-1C), both with and without a lipase inhibitor, to a dough sample. The effect is measured in terms of the per mille (‰) of free fatty acids remaining in the dough. Further reference to FIG. 1 may be found in the examples section.

Figure 2:
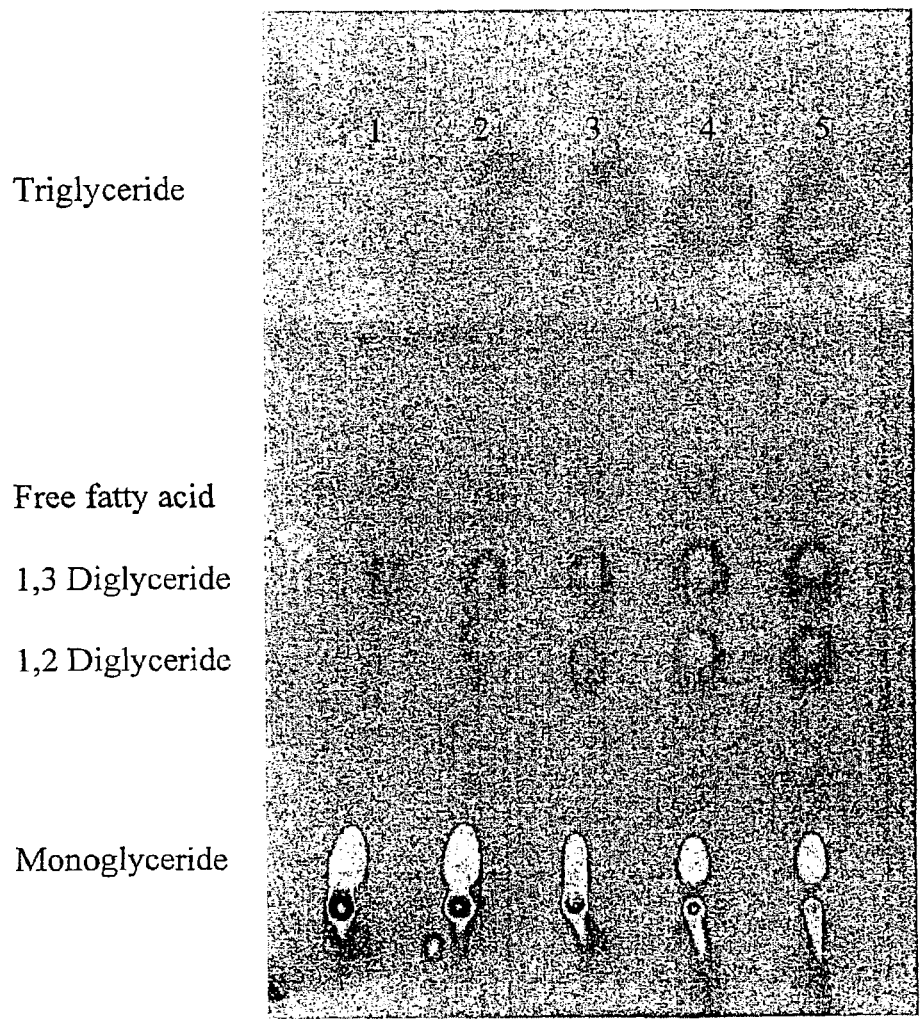

FIG. 2 shows a typical example (2135-135) of the TLC analysis of the solid phase glycerolysis reaction products, after eluting with P-ether: methyl-t-butyl-ketone (MTBK): acetic acid (70:30:1), staining in Vanadate solution and heating to 100° C.

EXAMPLES

Materials

Lipase: #2402 LIPOSAM *Pseudomonas* sp. Lipase.

*Chromobacterium viscosum* (batches #2405, #2450 and #2474) lipase from EUROPA-Bioproducts, UK.

Hardened Palm Stearin, 038500:

| Dropping point | app. 60° C. |
|---|---|
| F.F.A. | max. 1.0% |
| Iodine value | max. 2 |

Fractionated Palm Stearin: Palmotex 98T, Aarhus Olie, Denmark:

| Iodine value | 35 |
|---|---|
| F.F.A. | max. 0.1 |

Solid Fat Index

| 10° C. | 75-90 |
|---|---|
| 20° C. | 60-75 |
| 30° C. | 40-50 |
| 35° C. | 32-42 |

Hardened Palm Stearin, Grindsted PS 101:

| Dropping point | app. 60° C. |
|---|---|
| F.F.A. | max. 1.0% |
| Iodine value | max. 2 |

Powdered Lecithin, Stempur, Stern Lecithin & Soja GmbH & Co. KB, Hamburg:

| Acetone insoluble | min. 96% |
|---|---|
| Water | max. 1% |
| Acid value | max. 35 |

Soya Lecithin 003175:

| | |
|---|---|
| Acetone insoluble | min. 62% |
| Acid value | 20-28 mg KOH/g |
| Water max. | 1% |

Hydrolysed Lecithin: Lecithin H, 036702:

| | |
|---|---|
| Acid value | 28-45 mg KOH/g |
| Glycerol | 99.5% |

Methods
Thin Layer Chromatography (TLC)
Reaction products were analysed by TLC using Kieselgel F 60 plates from Merck.
Elution system: P-ether: MTBK: Acetic Acid 70:30:1
Development: Dipping in Vanadate solution followed by heating to 100° C.
Gas Chromatography
Perkin Elmer 8420 Capillary Gas Chromatography equipped with WCOT fused silica column 12.5 m×0.25 mm ID×0.1 μm 5% phenyl-methyl-silicone (CP Sil 8 CB from Crompack).

| | | | | |
|---|---|---|---|---|
| Carrier: | Helium. | | | |
| Injection: | 1.5 μl with split. | | | |
| Detector: | FID. 385° C. | | | |
| Oven program: | 1 | 2 | 3 | 4 |
| Oven temperature: ° C. | 80 | 200 | 240 | 360 |
| Isothermal, time, min. | 2 | 0 | 0 | 10 |
| Temperature rate, ° C./min. | 20 | 10 | 12 | |

Sample preparation: 50 mg lipid is dissolved in 12 ml heptane: pyridin 2:1 containing an internal standard of heptadecane, 2 mg/ml. 500 μl of sample is transferred to a crimp vial. 100 μl MSTFA (N-Methyl-N-trimethylsilyl-trifluoracetamid) is added and reacted for 15 minutes at 90° C.

Calculation: Response factors for mono-di-triglycerides and free fatty acid are determined from reference mixtures of these components. Based on these response factors, the mono-di-triglycerides, free fatty acids and glycerol in the sample are calculated.

Model Dough
10 gram Danish flour (Reform), 0.1 g dry yeast (LeSaffre), 0.3 g salt, and water to 500 Brabender Units (BU) are mixed in a mini Brabender Farinograph for 6 minutes. The dough is placed in a plastic beaker with lid for 60 minutes at 32° C. The dough is then frozen and freeze-dried.

Lipid Extraction and Fatty Acid Analyses
20 g of fully proofed dough was immediately frozen and freeze dried. The freeze-dried dough was milled in a coffee mill and passed through an 800 micron screen. 2 g freeze-dried dough was scaled in a 15 ml centrifuge tube with screw lid and 10 ml of water saturated butanol (WSB) was added. The centrifuge tube was placed in a boiling water bath for 10 minutes. The tubes were placed in a Rotamix and rotated at 45 rpm for 20 minutes at ambient temperature. The tubes were then placed in a boiling water bath again for 10 minutes and rotated on the Rotamix for 30 minutes at ambient temperature. The tubes were centrifuged at 3500 g for 5 minutes and 5 ml of supernatant was transferred into a vial. The WSB was evaporated to dryness under a steam of nitrogen.

The free fatty acids in the extract were analysed as Cu-salts in iso-octan measured at 715 nm and quantified according to a calibration curve based on oleic acid (Kwon, D. Y., and J. S., Rhee (1986), A Simple and Rapid Colourimetric Method for Determination of Free Fatty Acids for Lipase Assay, *JAOCS* 63:89).

Results
2133-134. Glycerolysis Reaction with Hardened Palm Stearin
Fully hardened palm stearin, fractionated palm stearin, and lipase dissolved in glycerol were spray crystallized. The recipe is shown below in table 1.

TABLE 1

| 2133-134- | | | 1 | 2 | 3 | 4 |
|---|---|---|---|---|---|---|
| Hardened Palm stearin, 038500 | | g | 500 | 500 | 500 | 400 |
| Palmotex T98 | | g | | | | 100 |
| Glycerol: lipase A | | g | 88 | 56 | | |
| Glycerol: lipase B | | g | | | 100 | |
| Glycerol: lipase C | | g | | | | 88 |
| | LIPU/g | | A | B | C | |
| Glycerol, 99.5% | | g | 150 | 100 | 100 | |
| #2402 | 276700 | g | 0 | 0 | 0.5 | |
| #2405 | 1900000 | g | 0.2 | 0.015 | 0 | |
| Water | | g | 6 | 4 | 4 | |

Procedure
Hardened Palm stearin was melted at 65° C. Lipase was dissolved in water followed by addition of the glycerol. The lipase/glycerol phase was added to the fat phase at 60° C. The mixture was stirred at 60° C. and then transferred to the spray vessel at 60° C. During strong mixing with a Turrax mixer, this mixture was spray crystallized using the "tunnel" spray technique. The tunnel spray technique is similar to spray crystallisation, with the modification that the melted fat is pumped through a spray nozzle into a tunnel where the fat crystallises into a powder. Samples were stored at 25° C. and 40° C., and a third sample was cycled between 25° C. and 40° C. After one and seven days of storage the samples were analysed by TLC.

TLC analysis revealed that sample no. 4 produced an unusually high level of monoglyceride. The samples were also submitted to GLC analysis (Table 2).

TABLE 2

| | 2133-134-1 (40° C.)/% | 2133-134-2 (40° C.)/% | 2133-134-3 (40° C.)/% | 2133-134-4 (40° C.)/% |
|---|---|---|---|---|
| Glycerol | 8.1 | 5.1 | 11.4 | 1.1 |
| Free fatty acid | 0.1 | 0.6 | 0.5 | 1.7 |
| Monoglyceride | 22.7 | 15.8 | 11.1 | 69.4 |
| Diglyceride | 32.8 | 21.4 | 20.6 | 23 |
| Triglyceride | 35.8 | 57 | 56.5 | 6.2 |

GLC analysis confirmed a rather high level of monoglyceride was formed in sample 2133-134-4 containing a mixture of fully hardened fat and palm stearin (Palmotex T98). The level of monoglyceride in sample 2133-1344 should be compared with 20-25% monoglyceride which is the equilibrium concentration of monoglyceride when the enzymatic glycerolysis takes place in liquid form.

These results also indicate that samples 1, 2 and 3 with only saturated fat (and no lecithin) produced rather low levels of monoglyceride compared to sample 4, thus confirming that it is necessary to have some unsaturated fat in the reaction mixture in order to obtain a high level of monoglyceride.

2133-135

Instead of unsaturated triglyceride, lecithin powder was added in different concentrations to fully hardened palm stearin (Table 3).

TABLE 3

| 2135-135- | | 1 | 2 | 3 | 4 | 5 |
|---|---|---|---|---|---|---|
| Hardened palm stearin, 038500 | g | 7 | 8 | 9 | 9.5 | 9.9 |
| Lecithin powder, 074793 | g | 3 | 2 | 1 | 0.5 | 0.1 |
| Glycerol | g | 2 | 2 | 2 | 2 | 2 |
| Lipase #2402 | g | 0.01 | 0.01 | 0.01 | 0.01 | 0.01 |
| Water | g | 0.05 | 0.05 | 0.05 | 0.05 | 0.05 |

Procedure

Hardened palm stearin and lecithin powder were melted at 65° C. Lipase was dissolved in water followed by the addition of glycerol. The lipase/glycerol phase was added to the fat phase at 60° C. and stirred for 1 hour at 60° C. The sample was then homogenised in an Ultra Turrax mixer and crystallized on an aluminum plate. Samples were stored at 25° C. and 40° C. and analysed by TLC after one and seven days.

TLC-analysis illustrated that a high level of monoglyceride was produced when powdered lecithin was combined with hardened palm stearin. This was also confirmed by GLC analyses of samples stored at 40° C. for seven days (Table 4.)

TABLE 4

| GLC analysis | 2133-135-1 % w/w | 2133-135-2 % w/w | 2133-135-3 % w/w |
|---|---|---|---|
| Glycerol | 4.9 | 4.8 | 7.5 |
| Free fatty acid. | 3.2 | 2.8 | 2 |
| Monoglyceride | 68.8 | 67.8 | 49.6 |
| Diglyceride | 10.2 | 12.5 | 15.5 |
| Triglyceride | 0.3 | 4.1 | 29.7 |

From Table 4 it is clear that lecithin powder improves the glycerolysis reaction of hardened palm stearin. The highest level of glycerolysis is obtained with 30% powdered lecithin in the fat phase.

2133-139. Test of Glycerol Level and Soya Lecithin Instead of Powdered Lecithin

The effect of the glycerol level for the glycerolysis reaction was tested with hardened palm stearin. Soya lecithin was tested instead of powdered lecithin (Table 5), as powdered lecithin is not always the best lecithin choice for certain food applications, for example frying margarine.

TABLE 5

| 2133-139 | | 3 | 4 |
|---|---|---|---|
| Fully hardened palm stearin | g | 8 | 8 |
| Soya lecithin | g | 2 | 2 |
| Glycerol/lipase A | g | 2 | 1 |
| | | A | |
| Glycerol 99.5% purity | g | 10 | |
| Lipase #2402 | g | 0.05 | |
| Water | g | 0.25 | |

These samples were prepared in the same way as mentioned above, and stored for seven days and analysed by GLC (table 6).

TABLE 6

| 2133-139 | 3 % w/w | 4 % w/w |
|---|---|---|
| Glycerol | 4.7 | 4.8 |
| Monoglyceride | 65.5 | 20.3 |
| Diglyceride | 21.7 | 30.2 |
| Triglyceride | 5.6 | 44.5 |

This experiment confirms that soya lecithin also promotes the glycerolysis of hardened palm stearin. The importance of having a sufficiently high level of glycerol level for the conversion to monoglyceride is also confirmed in this experiment.

2192-6 Testing Different Lipases for Solid Phase Glycerolysis

The glycerolysis reaction with lecithin powder and hardened palm stearin was repeated by producing the powder by a "tunnel" spray system. Both Lipase #2402 from *Pseudomonas* sp. and #2450 *Chromobacterium viscosum* were tested (Table 7).

TABLE 7

| 2192-6- | | 1 | 2 | 3 | 4 |
|---|---|---|---|---|---|
| Hardened Palm Stearin | g | 350 | 350 | 350 | 560 |
| Lecithin powder, 074793 | g | 150 | 150 | 150 | 140 |
| Glycerol | g | 100 | 100 | 75 | 105 |
| Lipase #2402 | g | 0.4 | | | 0.5 |
| Lipase # 2450 | g | | 0.1 | 0.05 | |
| Water | g | 2.5 | 2.5 | 2.5 | 3.5 |

Procedure

Hardened palm stearin and lecithin powder are melted together and cooled to 60° C. Lipase is dissolved in water and glycerol added. The lipase dissolved in glycerol is added to the fat phase and stirred at 55° C. for one hour. The mixture is homogenised by using a Turrax mixer and sprayed at 60° C.

Samples of the spray crystallized powder are stored at

A) 25° C.

B) 40° C.

C) Temperature cycles 35° C.-45° C.

After seven days of storage the samples were analysed by GLC (Table 8).

TABLE 8

| 2192-6- | 1B % | 2B % | 3B % | 4B % | 1C % | 2C % | 3C % | 4C % |
|---|---|---|---|---|---|---|---|---|
| Glycerol | 6.3 | 6.2 | 7.6 | 7.1 | 6.9 | 6.4 | 7.5 | 5.8 |
| Monoglyceride | 54.3 | 56.6 | 27.6 | 26.0 | 49.6 | 58.8 | 29.8 | 35.4 |
| Diglyceride | 24.1 | 19.7 | 36.9 | 46.3 | 27.9 | 23.9 | 42.0 | 34.0 |
| Triglyceride | 1.5 | 3.1 | 11.6 | 8.5 | 1.4 | 3.1 | 12.6 | 11.5 |

The results indicate that the level of monoglyceride is no higher for samples subjected to temperature cycles than for samples stored at 40° C.

Samples 3 and 4 contained a lower proportion of glycerol, and produced a lower level of the monoglyceride as before (Table 6).

2192-18 Testing Different Levels of Soya Lecithin

As powdered lecithin is not suitable for certain applications, the reaction was tested using normal soya lecithin instead. Samples for glycerolysis containing hardened palm stearin and soya lecithin were prepared as shown in Table 9.

TABLE 9

| 2192-18 | | 1 | 2 | 3 | 4 |
|---|---|---|---|---|---|
| Hardened palm stearin | g | 7.5 | 8 | 8.5 | 9 |
| Soya Lecithin | g | 2.5 | 2 | 1.5 | 1 |
| Glycerol, 99.5% | g | 2 | 2 | 2 | 2 |
| Lipase # 2450 | g | 0.002 | 0.002 | 0.002 | 0.002 |
| Water | g | 0.05 | 0.05 | 0.05 | 0.05 |

Procedure

Hardened palm stearin and soya lecithin are melted at 60° C. The lipase is dissolved in water and glycerol is added. The lipase/glycerol mixture is added to the fat phase at 55° C. and stirred for 10 minutes.

The sample is homogenised and crystallised and stored at
(A) 25° C. for seven days followed by temperature cycles 35° C.-45° C. for 12 hours.
(B) 40° C. for seven days
The samples were analysed by GLC (Table 10).

TABLE 10

| 2192-18- | 1A % w/w | 2A % w/w | 3A % w/w | 4A % w/w | 1B % w/w | 2B % w/w | 3B % w/w | 4B % w/w |
|---|---|---|---|---|---|---|---|---|
| % Glycerol | 3.4 | 3.2 | 2.9 | 3.4 | 3.3 | 2.5 | 1.9 | 1.4 |
| % FFA | 1.2 | 1.1 | 0.4 | 0.4 | 1.1 | 0.5 | 0.4 | 0.3 |
| % Monoglyceride | 78.6 | 77.3 | 80.5 | 75.2 | 79.6 | 81.8 | 86.2 | 85.9 |
| % Diglyceride | 4.6 | 4.6 | 2.6 | 3.3 | 5.3 | 3.9 | 2.8 | 1.9 |
| % Triglyceride | 2.4 | 7.3 | 7.1 | 15 | 2.2 | 3.4 | 3 | 7 |

These results indicate a significant improvement in the level of monoglyceride obtained by glycerolysis when soya lecithin is used instead of powdered lecithin. It is also noticeable that samples 3 and 4, with the lowest levels of lecithin, gave the highest level of monoglyceride, and the results confirm that only small amounts of soya lecithin are needed in order to obtain a high conversion of hardened fat to monoglyceride by solid phase glycerolysis.

2192-22 Testing Different Types of Lecithin

Experiment 2192-18 was repeated on larger scale by "tunnel" spraying, and both soya lecithin and hydrolysed lecithin (Lecithin H) were tested (Table 11).

TABLE 11

| 2192-22- | | 1 | 2 |
|---|---|---|---|
| Grindsted PS 101 | g | 425 | 450 |
| Soya lecithin | | 75 | |
| Lecithin H | g | | 50 |
| Glycerol | g | 100 | 100 |
| Lipase # 2450 | g | 0.1 | 0.1 |
| Water | g | 2.5 | 2.5 |

Procedure

Grindsted PS 101 and lecithin were melted at 70° C. Lipase was dissolved in water and glycerol added. The lipase/glycerol phase was added to the fat phase at 60° C. The sample was then homogenised for 5 minutes and spray crystallised using a "tunnel" spray technique. Samples were stored at 25° C. and 40° C. During storage, samples were taken out after one, two, and six days and analysed by TLC. After seven days of storage samples stored at 40° C. were analysed by GLC (Table 12).

TABLE 12

| 2192-22 | 1 % w/w | 2 % w/w |
|---|---|---|
| Glycerol | 2 | 1.9 |
| FFA | 1.9 | 1.9 |
| Monoglyceride | 84.5 | 83.6 |
| Diglyceride | 6.4 | 8.7 |
| Triglyceride | 0.7 | 1.2 |
| Total | 95.6 | 97.4 |

The results in table 12 confirm that it is possible to use both Soya Lecithin and Lecithin H in combination with hardened palm stearin for making high levels of monoglyceride by glycerolysis in powder form.

2192-37 Solid Phase Glycerolysis Containing a Carrier for Glycerol

In this experiment lipase *Chromobacterium viscosum* #2474 was used as a catalyst for solid phase glycerolysis of fully hydrogenated palm stearin, Grindsted PS 101 combined with 7.5% soya lecithin. Instead of soya lecithin, 10% fractionated palm stearin, Palmotex T98, was tested in combination with Grindsted PS 101. At this concentration of Palmotex T98, a powder could easily be obtained from the recipe by spray crystallisation.

One of the limitations of using spray crystallisation of fat, followed by solid phase glycerolysis, is that glycerol makes the powder a little greasy. This may be eliminated by adding a solid carrier for the glycerol which acts as a delivery system for the glycerol. In the following experiment, sugar beet fibre FIBREX was added in order to test this theory. The recipe for the experiments is shown below in Table 13.

TABLE 13

| | | 1 | 2 | 3 |
|---|---|---|---|---|
| Grindsted PS 101 | g | 462.5 | 450 | 450 |
| Soya lecithin | g | 37.5 | | 50 |
| Fibrix | g | | | 60 |
| Palmotex T 98 | g | | 50 | |
| Glycerol | g | 100 | 100 | 100 |
| Lipase # 2474 | g | 0.05 | 0.05 | 0.05 |
| Water | g | 2.5 | 2.5 | 2.5 |

The samples were prepared according to the following procedure:

Grindsted PS 101 and soya lecithin or Palmotex T98 were melted together and cooled to 60° C. Lipase #2474 was dispersed in water and glycerol added. The Fibrex was added prior to spray crystallisation. The mixture was homogenised by Ultra Turrax mixing followed by spray crystallisation. The sample was stored at 40° C. for seven days and analysed by GLC.

The results from the GLC analysis are shown in Table 14.

TABLE 14

|  | 1 | 2 | 3 |
|---|---|---|---|
| % Glycerol | 1.6 | 4.6 | 4.4 |
| % Free fatty acid | 0.9 | 1.1 | 1.7 |
| % Monoglyceride | 89.2 | 62.2 | 59.4 |
| % Diglyceride | 4.6 | 15.2 | 13.5 |
| % Triglyceride | 0.8 | 20.8 | 13.2 |

Table 14 confirms that very efficient solid phase glycerolysis of fully hydrogenated Palm Stearin may be achieved by adding 7.5% soya lecithin and using *Chromobacterium viscosum* lipase as a catalyst.

The results also confirm that when soya lecithin is substituted by partially saturated fat, the solid phase glycerolysis is less efficient. Furthermore, adding a sugar beet fibre, such as Fibrix, decreases the degree of glycerolysis. This effect may be attributable to the competition for water in the reaction mixture, which makes the enzyme less efficient.

2192-39 Lipase Inhibition

The solid phase glycerolysis product is intended for use in baking and other applications. However, the lipase is still active when added to the dough and for certain applications, the level of lipase activity may be too high and cause adverse effects.

In order to investigate this further, an experiment was carried out to investigate the effect of combining the solid phase glycerolysis product 2192-6-1C with a lipase inhibitor in a dough system. Initial tests have shown that ferrichloride is an efficient inhibitor for certain lipases.

Model dough was made according to the recipe above and with the additions shown in Table 15. The dough was extracted with water-saturated butanol and the amount of free fatty acid determined.

TABLE 15

|  |  | 1 | 2 | 3 |
|---|---|---|---|---|
| Solid phase glycerolysis 2192-6-1C | % | 0 | 0.5 | 0.5 |
| Ferrichloride, 2% solution in water. | % | 0 | 0 | 1 |

The results from the fatty acid analysis are shown in FIG. 1. The results indicate that it is possible to combine a solid phase glycerolysis product with a lipase inhibitor and reduce the activity of the lipase activity in the dough.

Various modifications and variations of the described methods and system of the invention will be apparent to those skilled in the art without departing from the scope and spirit of the invention. Modifications of the described modes for carrying out the invention which are obvious to those skilled in chemistry or related fields are thus intended to fall within the scope of the following claims.

I claim:

1. A process for preparing an enzymatic solid phase reaction mixture for preparing a solid having greater than 40% monoglyceride, said process comprising:
   (i) melting a triglyceride derived from palm oil, sunflower oil, rape seed oil, soya bean oil, safflower oil, cottonseed oil, ground nut oil, corn oil, olive oil, peanut oil, lard, tallow, or mixtures thereof, with a lecithin, to form a fat phase;
   (ii) adding to said fat phase a solution of lipase in glycerol, wherein the glycerol is present in an amount of at least 14% by weight of the total mixture, and stirring the resultant mixture;
   (iii) homogenizing said mixture; and
   (iv) processing said enzymatic solid phase reaction mixture by (a) spray crystallizing or (b) pelleting, flaking or extruding and grinding.

2. The process according to claim 1 wherein the triglyceride is hardened palm stearin.

3. The process according to claim 1 wherein the lecithin is selected from plant lecithin or powdered lecithin.

4. The process according to claim 1 wherein the lipase is derived from *Pseudomonas* sp., *Chromobacterium viscosum, Pseudomonas cepacia, Pseudomonas stutzeri, Pseudomonas flourescens, Mucor miehei* or *Candida antartica*.

5. The process according to claim 1 wherein the lecithin is present in an amount from about 1% to about 50% by weight.

6. The process according to claim 1 wherein the triglyceride is present in an amount from about 1% to about 86% by weight.

7. The process according to claim 1 wherein glycerol is present in an amount from about 14% to about 25% by weight.

8. The process according to claim 1 wherein the enzymatic solid phase reaction mixture is spray crystallized.

9. The process according to claim 1 wherein a solid carrier for the glycerol is added to said reaction mixture.

10. The process according to claim 9 wherein said solid carrier for the glycerol is sugar beet fibre.

11. The process according to claim 1 wherein processing of the enzymatic reaction mixture is by pelleting, flaking or extruding and grinding.

* * * * *